United States Patent [19]

Gordinier et al.

[11] Patent Number: 5,599,558
[45] Date of Patent: Feb. 4, 1997

[54] SELECTING AMOUNTS OF PLATELET RELEASATE FOR EFFICACIOUS TREATMENT OF TISSUE

[75] Inventors: Richard H. Gordinier, Centereach; Ronald G. Duff; Dawn D. Newmann, both of East Moriches, all of N.Y.

[73] Assignee: Curative Technologies, Inc., East Setauket, N.Y.

[21] Appl. No.: 328,651

[22] Filed: Oct. 25, 1994

Related U.S. Application Data

[63] Continuation of Ser. No. 822,286, Jan. 16, 1992, abandoned, which is a continuation-in-part of Ser. No. 408,058, Sep. 15, 1989, abandoned.

[51] Int. Cl.$^6$ .................... A61K 35/14; A61K 43/00; A61K 35/12; G01N 33/00
[52] U.S. Cl. ................ 424/532; 514/2; 514/21; 514/773; 514/802; 514/886; 514/887; 530/351; 530/380; 530/381; 530/382; 530/383; 530/384; 530/399; 530/829; 530/830; 424/520; 424/529; 436/503
[58] Field of Search .................... 424/532, 520, 424/529; 436/503; 514/2, 21, 773, 802, 886, 887; 530/351, 380, 381, 382, 383, 384, 399, 829, 830

[56] References Cited

U.S. PATENT DOCUMENTS

| | | |
|---|---|---|
| 4,195,072 | 3/1980 | Workman, Jr. . |
| 4,298,598 | 11/1981 | Schwartz et al. . |
| 4,503,038 | 3/1985 | Banda ................. 424/537 |
| 4,760,131 | 7/1988 | Sundsmo et al. . |

FOREIGN PATENT DOCUMENTS

| | | |
|---|---|---|
| 0007163 | 1/1980 | European Pat. Off. . |
| 0308717 | 3/1989 | European Pat. Off. . |
| 0325224 | 7/1989 | European Pat. Off. . |
| 0325723 | 8/1989 | European Pat. Off. . |
| 0202298 | 7/1992 | European Pat. Off. . |
| 8603122 | 6/1986 | WIPO . |

OTHER PUBLICATIONS

Newman, J Cell Biochem Suppl 0 (14 Part E). 1990. 253 Abstract #Q210.
Grotendorst, Intl J Tiss Reac X(6) 337–344 (1988).
Takahashi, Clinica Chimica Acta 175 (1988) 113–114.
Nagelschmidt, et al J of Trauma vol. 27, No. 11 pp. 1267–1272.
Knighton, et al Ann Surgery 1986 pp. 322–330.
Figdor, Advances in Neuroblastoma Research, pp. 459–470, Liss, ed. (1985).
Greaves, Clin. Exp. Dermatol. 5:101–103 (1980).
Grotendorst, "Growth Factors as Regulators of Wound Repair", Int'l J. Tissue React. X(6):337–344 (1988).
Grotendorst, J. Trauma 24 (suppl. 9):49–54 (1984).
Knighton, Annals of Surgery 196(4):379–388 (1982).
Knighton et al., Annals of Surgery 204(3):322–330 (1986).
Michaeli et al., Surgical Science Series, vol. 2, pp. 380–394 (1984).
Nagelschmidt et al., J. of Trauma 27(11):1267–1272 (1987).
Newman, J. Cell Biochem. 253 Suppl. 0 (14 part E):Abstract Q210 (1990).
Rasanen, J. Leukocyte Biology 43:343–348 (1988).
Takahashi, Clin. Chim. Acta. 175:113–114 (1988).
Thornton, Burns 8:156–160 (1981).

*Primary Examiner*—Esther Kepplinger
*Assistant Examiner*—Choon Park Koh
*Attorney, Agent, or Firm*—Thomas E. Popovich

[57] ABSTRACT

A method of making a platelet releasate product is disclosed involving performing an assay on a platelet releasate sample for a component of the releasate and forming platelet releasate product by comparing the assay results to a predetermined range of amounts of the component to be contained in the product. A method of treatment of tissue is disclosed involving the topical application of such product.

13 Claims, 6 Drawing Sheets

SELECTING AMOUNTS OF PLATELET RELEASATE FOR EFFICACIOUS TREATMENT OF TISSUE

FIELD OF THE INVENTION

This is a continuation of application Ser. No. 07/822,286, filed Jan. 16, 1992, now abandoned, which is a continuation-in-part of application Ser. No. 07/408,058 filed Sep. 15, 1989, now abandoned. This invention relates to selecting amounts of platelet releasate for efficacious treatment of tissue.

BACKGROUND OF THE INVENTION

Tissue repair or "wound healing" involves many cellular and biochemical reactions which transform quiescent connective tissue and epidermal cells into rapidly dividing, rapidly moving cells. This transformation involves chemotaxis (movement of cells), mitogenesis (division of cells), and increased protein synthesis. Epidermal cells, fibroblasts, and capillary endothelial cells are involved in the formation of new tissue. Epidermal cells migrate and divide to form new skin (epithelium) at the site of tissue repair; fibroblasts move and divide to produce the matrix which fills the repair site (granulation site); capillary endothelial cells migrate and divide to produce new capillaries which revascularize the fibroblast/collagen matrix.

The process of cellular migration and mitosis is under the control of several biochemical agents. These locally-acting agents act on the various cells to direct their movement and division.

Each of these biochemical agents is (1) chemotactic (i.e., a chemoattractant) and causes migration (chemotaxis) of a certain type of cell; (2) mitogenic (i.e., a mitogen) and causes division (mitogenesis) of a certain type of cell; and/or (3) angiogenic (i.e., an angiogenic factor) and causes formation of new capillaries (migration and division of capillary endothelial cells). The chemotactic, mitogenic or angiogenic character of a biochemical agent is generally determined by testing the agent in various known assays for chemotaxis, mitogenesis and anglogenesis. Some of these assays are described below. Additional assays are expected to be developed in the future which will be directed at the same characteristics but perhaps will more clearly define or measure the presence of the characteristic.

Platelet-Derived Growth Factor (PDGF) is a well-characterized, 30,000 dalton dimeric glycoprotein with mitogenic and chemoattractant activity for fibroblasts, smooth muscle cells and glial cells. In the presence of PDGF, fibroblasts move into the area of tissue needing repair and are stimulated to divide in the wound space itself. The cells exposed to lower PDGF concentrations (approximately 0.5–1 ng/ml) are stimulated to move and, as they move to environments having higher concentrations of PDGF (approximately 1–2 ng/ml), they are stimulated to divide.

The process of neovascularization or angiogenesis (new capillary formation) is stimulated by angiogenesis factors. The angiogenesis factor recoverable from platelets (PDAF) is a pure chemoattractant without mitogenic activity for capillary endothelial cells, which stimulates them to move through a gradient towards the source of the angiogenesis factor. Once the capillary cells start to move from the parent capillaries, they start to divide. This division is probably under the control of autocrine growth factors produced by endothelial cells, which have been found to be of the basic fibroblast growth factor (FGF) variety.

The combination of fibroblast migration and mitosis and endothelial cell migration and mitosis produces granulation tissue. Granulation tissue also is rich in neutrophils and monocytes which have been brought to the site of repair by the presence of C5A from complement activation and transforming growth factor beta (TGF-B) from platelets. The presence of these phagocytic cells decreases the contamination and prevents overt infection.

TGF-B is a 25,000 dalton (112 amino acid) polypeptide that has a function in the synthesis of fibrin-collagen. TGF-B inhibits the division of fibroblasts and increases their matrix production. Whether TGF-B stimulates or inhibits division is a function of the entire set of growth factors operating in the tissue. In the presence of PDGF, TGF-B usually stimulates division while it usually inhibits division in the presence of epidermal growth factors (described below).

After granulation tissue is formed, epidermal cells migrate from the cut skin edge over the granulation tissue to form a new skin layer, which then matures into normal skin. This cellular activity is at least partially under the control of platelet-derived epidermal growth factor (PDEGF) which is a chemoattractant for epidermal cells.

In summary, the process of tissue repair or "wound healing" is under the control of at least four growth factors: TGF-B, PDGF, PDAF and PDEGF. The presence of these growth factors in the tissue to be repaired produce fibroblast migration and mitosis, endothelial cell migration and subsequent mitosis, and epidermal migration and mitosis. The end result is the filling of wound space with a granulation tissue followed by reepithelialization and skin maturation.

Two principal sources of these factors for natural healing of tissue are platelets and macrophages. When tissue is damaged in the body, platelets are released by the presence of thrombin generated by the activation of the coagulation process. These platelets then release PDGF, PDAF, PDEGF, TGF-B and platelet factor 4 (PF-4 is a chemoattractant for neutrophils and monocytes) and stimulate release of complement C5A. The PDGF, PDAF, PDEGF and PF-4 themselves contribute directly to healing the wound as described above, while TGF-B and C5A attract macrophages to the damaged site. Macrophages also release same or similar mitogens, chemoattractants, and angiogenesis factors once they have been summoned to the area of tissue repair. However, to date, macrophages are not known to produce EGF-like activity.

Common reasons for the failure of nonhealing wounds to improve are: infection, poor cellularity, few fibroblasts, no new capillaries and few inflammatory cells. In contrast, healing wounds are characterized by mononuclear and macrophage cell infiltrates, dividing fibroblasts and numerous capillaries.

Knighton, et al, Ann. Sur. 1986, 204:322–330, incorporated in its entirety herein by reference thereto, treated 49 patients with chronic nonhealing cutaneous ulcers using autologous Platelet Derived Wound Healing Formula (PDWHF) in a microcystalline collagen salve. The wounds had been treated an average of 198 weeks with conventional treatment. Mean healing time to 100% epithelization was 10.6 weeks direct correlation to 100% healing was related to initial wound size and initiation of PDWFIF therapy. There was no abnormal tissue formation, keloid or hypertrophic scarring reported.

In a double-blind study, Knighton et al, Tissue Repair Symposium at Tarpon Springs, Florida May 1987, which is incorporated herein in its entirety by reference thereto, compared wound healing using PDWHF in a collagen base to a placebo. All 24 patients received wound care according to a standard protocol. The 13 patients in the PDWHF group had healing to 100% epithelization in 17 or 21 wounds after 8 weeks of therapy; of 11 patients in the placebo group only 2 of 13 had wounds that reached 100% epithelization. The 5 placebo failures were then treated with PDWHF and their wounds healed in an average of 7.1 weeks. The unhealed PDWHF treated patients continued on PDWHF and achieved 100% epithelization in an average of 5.8 additional weeks of treatment.

The pretreatment records for a group of patients seen at the University of Minnesota Wound Care Clinic were provided to a panel of three nationally recognized experts in amputation, diabetic foot care and vascular surgery. The 136 wounds in 73 patients were graded on a severity scale of 1 through 6 (partial thickness to full thickness with gangrene). PDWHF therapy had been initiated in each case. Over 75% had wound grades of 3 or higher. Seventy (70%) of the limbs evaluated were considered to be at significant or definite risk of amputation. Of the 26 limbs scored at no risk of amputation, none required amputation. Over 90% of the 53 limbs considered to be at significant risk of amputation were salvaged. Limbs scored at requiring immediate amputation (n=9) had a salvage rate of 86%. Applying PDWHF to wounds on a daily basis promoted granulation tissue formation and epidermal cell growth stimulation. Chronic non-healing wounds have been healed to fully functional skin.

In the foregoing studies of wound treatment, the PDWHF formulation was based on releasing $10^9$ platelets into medium to a final volume of 1 ml. No attempt was made to adjust the amount of platelet releasate to compensate for variation from donor to donor, or from time to time for a particular donor, of the potencies of the wound healing factors contained in such platelet releasate. It is an object of the present invention to select amounts of platelet releasate for efficacious treatment of tissue, giving due regard to variations of the potencies of healing factors contained in the releasate.

BRIEF SUMMARY OF THE INVENTION

In accordance with the invention, tissue may be treated by applying topically a platelet releasate product containing a selected amount of platelet releasate. The platelet releasate product preferably is applied to tissue to be treated in an amount sufficient to cause, if desired, migration and/or division of fibroblasts, capillary endothelial cells and/or epidermal cells such that the division or migration of the cells contributes to the formation of granulation tissue, capillaries and/or epithelium in the area of treatment.

The present invention provides a method for making a platelet releasate product useful in treatment of tissue. An assay is performed on a platelet releasate sample, where the assay indicates the amount of a component present in the platelet releasate sample. The "component" preferably is a wound healing factor or its amount correlates to the amount of desired wound healing factors present in platelet releasate. The assay may be an immunoassay for detecting the amount or presence of such components or may be any other method for determining the presence or amount of the component such as the use of HPLC. Based on the results of the assay, a platelet releasate product is formed which contains a selected amount of platelet releasate. The amount is selected by comparing the amount of the component in the platelet releasate sample to a predetermined range of amounts of the identical component to be contained in a releasate product. The present invention further provides a method of treating tissue whereby the foregoing releasate product is applied topically to tissue.

An alternative method of making a platelet releasate product, and topical application of such product to tissue, involves performing an assay on a platelet releasate sample, where the assay indicates the amount of an activity of the platelet releasate sample.

The platelet releasate contained in the platelet releasate product and in the platelet releasate sample is preferably obtained from the same draw of platelets. Alternatively, the platelet releasate contained in the platelet releasate product and in the platelet releasate sample may be obtained from different draws of platelets from the same animal or human. As a further alternative, the platelet releasate contained in the platelet releasate product and in the platelet releasate sample may be obtained from a pool of platelets taken from singular or multiple draws of platelets from a single animal or human or from a group of animals or human donors.

The range of the amount of the component to be contained in a platelet releasate product may be predetermined so that the selected amount of platelet releasate contained in said platelet product is sufficient to cause substantial efficacy of treatment of tissue in a chosen percentage of treatments. For example, such treatment efficacy may be chosen to obtain at least a grade 2 functional assessment score, hereinafter defined, in greater than 50% of wounds treated. Alternatively, a range of amounts of an activity of platelet releasate product may be similarly based on a desired efficacy of treatment of tissue.

The components, for which a range of amounts is predetermined for such efficacy, may be Beta-thromboglobulin ("B-TG"), PDGF, PDAF, PF-4, basic FGF, acidic FGF, TGF-$\alpha$, TGF-B, PDEGF and fibronectin. The activity may be fibroblast mitogenic activity ("FMA"), endothelial cell chemotaxis activity ("ECCA"), rabbit corneal assay activity ("RCAA") or keratinocyte cell chemotaxis activity ("KCCA").

Finally, the platelet releasate may be combined with a pharmaceutically acceptable carrier or diluent for such platelet releasate to form a platelet releasate product. Further, the product may be substantially free of blood or plasma contaminants and free of platelet ghosts or other materials contained in the platelets but not released by platelets.

"Treatment" includes wound healing, cosmetic or any other process in which it is desirable to promote angiogenic, mitogenic or chemotactic activity in the region of the tissue to be treated. Possible treatment applications of tissue include, without limitation, any of those listed in Table 1. Such treatments are topical in the sense that they apply a composition to the surface of a region or body of tissue, but re not applied systemically.

Table 1

Potential Applications for Treatment of Tissue

I. Treatment of chronic non-healing cutaneous wounds
A. Ischemic wounds
1. Diabetic wounds
2. Ischemic wounds from atherosclerosis
3. Wounds from arteriolar vasculitis
B. Venous stasis wounds
1. Post-phlebitic syndrome
2. Post-traumatic venous stasis C. Pressure sores
  1. Sacral decubitus
  2. Ischial decubitus
  3. Heel and malleolar decubitus
  4. Other areas of pressure
  D. Wounds from persisting cutaneous trauma
II. Topical treatment of acute wounds
  A. Split thickness wounds
    1. Skin graft donor sites
    2. Abrasions such as those occurring from a motorcycle accident
  B. Full thickness skin loss
    1. Degloving injury
    2. Traumatic skin loss
    3. Traumatic skin necrosis
III. Burns
  A. Split thickness skin graft donor site repair
  B. Accelerating of granulation tissue formation and early debridement and grafting of skin
  C. Accelerating of re-epithelization of second degree burns
  D. Improvement of cosmetic result in skin grafting by prevention of chronic contracture
IV. Revascularization of intact skin
  A. Necrobiosis lipoidica diabeticorum
  B. Radiation induced skin ischemia
  C. Phemphigus vulgaris
V. Cosmetic applications
  A. Hair Growth
  B. Skin renewing preparation
  C. Wrinkle treatment
VI. Treatment of acute surgical wounds
  A. When combined with a slow-release biodegradable delivery system, compositions may enhance the rate of normal wound repair by shortening the lag phase. The delivery system may apply compositions topically to any surgical wound, either in the skin, fissures or internal organs.
VII. Internal surgical applications
  A. Compositions may be used to accelerate repair of internal surgical or traumatic wounds, including without limitation liver lacerations, kidney lacerations, splenic lacerations and anastomoses of, for example, the bowel, colon, or biliary tree
  B. Topical administration to internal wounds such as traumatic wounds of the liver and spleen
  C. Compositions may be applied to intra-abdominal abscesses to accelerate repair. For example, when an intra-abdominal abscess is drained percutaneously and the drain is left in place, compositions could be injected through the drain so as to topically apply the composition to the surfaces of the cavity to accelerate repair of that potential space.
VIII. Veterinary applications
  A. Accelerate surgical repair
  B. Accelerate repair of chronic non-healing wounds such as those of horses
  C. Accelerate repair of horse long bone fractures
  D. A system could be devised to deliver compositions to treat wounds in cattle to keep the contraction process from occurring and closing off the mammary duct
IX. Opthalmologic applications
  A. Accelerate healing of corneal ulcers
  B. Accelerate healing of corneal transplants
  C. Accelerate healing of other types of opthalmologic surgery
X. Orthopaedic applications
  A. Accelerate normal fracture healing
  B. Stimulate repair of non-unions
  C. Facilitate bone graft healing
  D. Stimulate repair after of teomyelitis debridement
  E. Compositions could be combined with prosthetic material (such as joint replacement) to accelerate tissue in growth
  F. Accelerate repair of tendon and ligament injuries
  G. Stimulate incorporation of artificial tendons
XI. ENT applications
  A. Accelerate repair of mastoidectomy wounds (which could be accomplished by topical administration similar to that done presently for chronic non-healing wounds)
  B. Combined with artificial prostheses (such as tympanic membranes, tympanic membrane tubes, or artificial eustachian tubes)
XII. Plastic surgical applications
  A. Control tissue remodeling (fill tissue defects with new tissue)
  B. Stimulate ingrowth into prosthesis (i.e. breast implants)
  C. Stimulate accelerated repair in flaps
  D. Since the scar which results from the topical administration of compositions is much more cosmetically satisfactory than an unstimulated scar, the material could be used topically in scar revision
  E. Accelerate repair of tendon injuries such as those occurring in the hand
XIII. Dental
  A. Accelerate repair of dry sockets
  B. Accelerate normal socket repair
  C. Accelerate ingrowth into dental implants
  D. Stimulate gum growth at the tooth bone line
XIV. Gastrointestinal applications
  A. When combined with the drug such as Sucralfate, compositions may accelerate the repair of stomach and duodenal ulcers
  B. Compositions may accelerate repair of ulcerative colitis in the colon when given as an enema
  C. Compositions may accelerate repair of granulomatous colitis when given orally in a slow-release material
XV. Vascular surgery
  A. Compositions (and especially angiogenesis factor) when combined with an arterial graft, may stimulate new vaso vasora to form which would re-endothelize the graft from the capillary ingrowth
XVI. Artificial endocrine organ
  A. The angiogenesis factor may be used to stimulate recapillary ingrowth into tubes in an artificial endocrine organ which could be implanted into the body. The capillaries would be stimulated to grow through the tubes and the cells or islets could be grown on the outside of the tubes to allow use of a totally xenographic endocrine system
XVII. Stricture formation
  A. Compositions may be combined with stents which are now being used in the esophagus, biliary tree, urethra, and ureters to stimulate angiogenesis and healing of a stented tubular structure which then decreases the restricture formation rate. The compositions may be delivered on the stent in a slow-release form such that the compositions are topically applied to the tissue surfaces surrounding the stent Uses for compositions of the present invention include, without limitation, any of those listed in Table 1 of 1A.

Table 1A

Additional Potential Applications for Compositions of the Present Invention

I. Revascularization of myocardial infarctions

A. Compositions may be injected into the center of a myocardial infarction by cardiac catheterization or percutaneously guided by magnetic resonance imaging in a slow-release system and accelerate infarct repair B. Compositions may be targeted with liposomes coated with anti-denatured collagen antibodies and given intravenously for migration to the site of a wound or myocardial infarction.

II. Revascularization of neural injuries

A. Compositions may be injected into a cerebral infarct or spinal cord injury in a slow-release system to accelerate repair B. As in I above, targeted liposomes carrying compositions may be used intraveneously with anti-denatured nerve antibodies to migrate to the site of a neurologic injury A chemical species has "chemotactic activity", "mitogenic activity" or "angiogenic activity", as those terms are used throughout this specification and the appended claims, when such species exhibits a positive response in the corresponding assays for angiogenesis, mitogenesis and chemotaxis described herein or similar assays available in the art or as later developed.

DETAILED DESCRIPTION OF THE INVENTION

Figure 1:
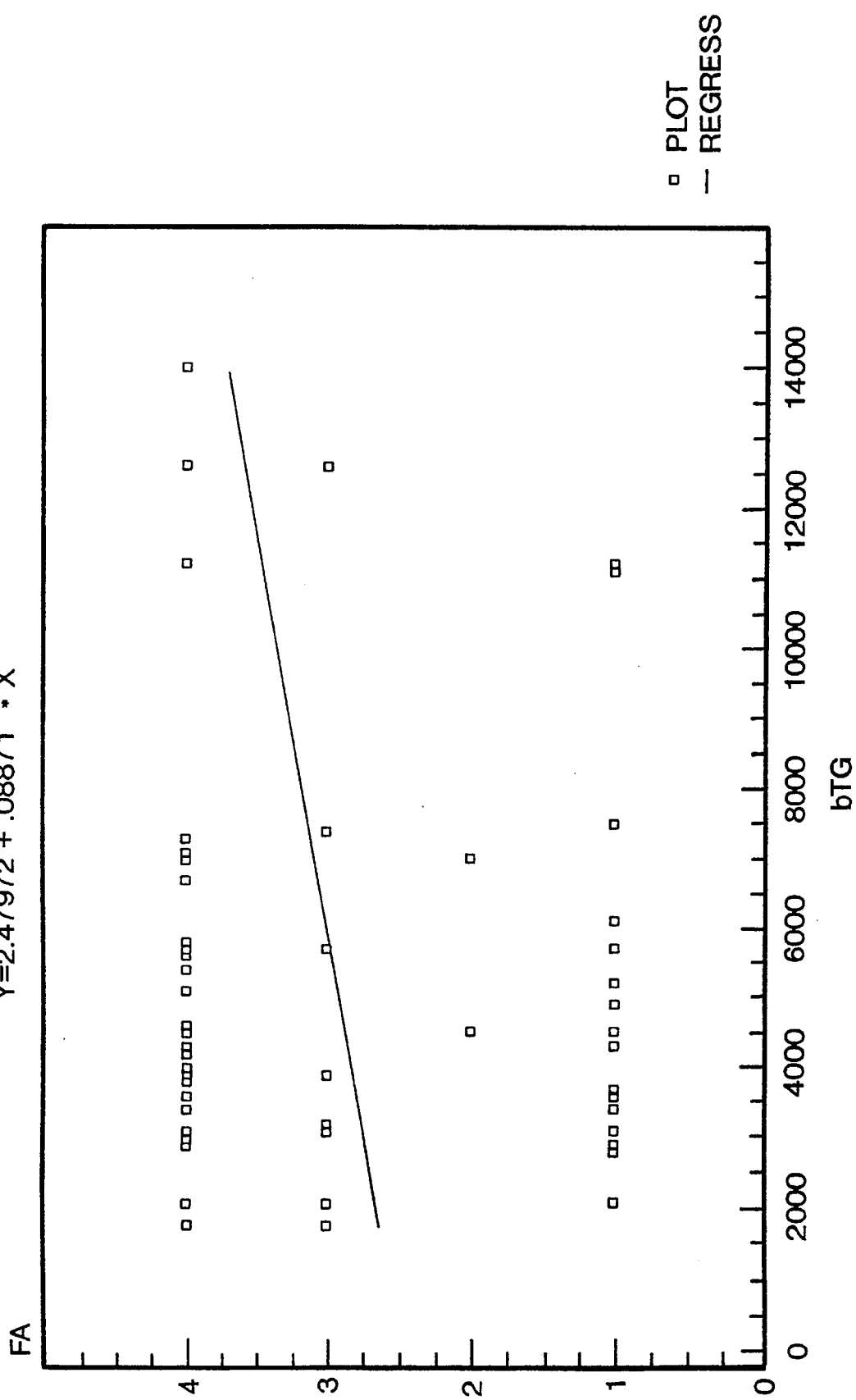
FIG. 1 shows a plot of functional assessment versus ng/ml of B-TG in platelet releasate extract in a Florida study.

Efficacy of treatment of tissue has been defined for chronic nonhealing cutaneous wounds. Functional assessment grades 1–4 measure wound healing maturity based on the following ratings:

(1) less than 100% epithelized; has drainage; needs a dressing.

(2) 100% epithelized; has drainage; needs a dressing for drainage control.

(3) 100% epithelized; maturing skin with small amount of drainage; requires protective dressing only.

(4) 100% epithelized; 100% mature functional skin; does not require a dressing.

The preferred procedure for treatment of chronic nonhealing cutaneous wounds involves applying the platelet releasate product once a day, at the same time each day. The product should remain on the wound for at least eight hours before it is rinsed off. During the other 12 hours, when the product is not on the wound, saline wet to dry dressing should be applied to the area.

While it is preferred to prepare platelet releasate product for wound treatment purposes directly from a patient's own blood, the advantages of the invention may be achieved by using blood or outdated platelets from other sources. Using a patient's own blood is disclosed since it avoids exposure of the patient to possible hepatitis, AIDS or other contaminants from banked blood. Using a patient's own blood also eliminates most allergic reactions to foreign blood. An alternative source of the product may, however, be obtained from pedigree blood (i.e. for persons screened for hepatitis, AIDS, etc.) or from outdated human platelets, and either from a single source or a pool of a plurality of sources. Blood from other species may also be used for human application. Finally, platelet product may also be utilized in veterinary applications by utilizing platelets derived from the animal itself, from another animal within the same species, or from another species.

EXAMPLE 1

60 ml whole blood was aeseptically obtained from a source in 6 ml of acid citrate dextrose anti-coagulant (hereinafter ACD), or 1 ml ACD per 10 ml of whole blood. The blood was mixed well with ACD by inverting and rolling the syringe. Anti-coagulated blood samples were kept on ice until used in further processing.

The anti-coagulated blood was transferred to two sterile, siliconized 50 ml conical-bottom centrifuge tubes, evenly splitting the sample between tubes. The tubes were then centrifuged at 135×g for 20 minutes at about 4° C. Upon completion of the centrifugation cycle, the rotor was allowed to coast to a stop. No braking was applied. The uppermost layer of the centrifuged sample, platelet-rich plasma (hereinafter PRP), was carefully transferred with a sterile pipette to another sterile, siliconized centrifuge tube. Drawing only 4–5 ml at a time minimized losses due to red blood cell contamination of the PRP. A platelet count of the PRP was then conducted using methods well known in the art.

The PRP was centrifuged at 750×g for 10 minutes at about 4° C. The supernatant was discarded, being careful not to dislodge the platelet pellet. Using a sterile pipette, the pellet was resuspended by aspirating and expelling buffer containing 0.05M HEPES (N-2-hydroxyethyl piperazine-n-2-ethane sulfonic acid), 0.03M dextrose, 0.004M KCl, 0.1M NaCl, pH adjusted to approximately 6.5 at 28° C. (hereinafter platelet buffer) to an approximate concentration of $10^9$ platelets per ml of suspension.

The resulting platelet suspension was then activated with purified thrombin. Preferably, about 1 unit of thrombin per ml of platelet suspension was added to the platelet suspension and mixed. The platelets and thrombin were allowed to incubate at room temperature for about 10 minutes. After incubation, the resulting platelet aggregate was broken up by aspirating and expelling the suspension with a sterile pipette.

Alternatively, the platelet suspension may be activated with other activators that cause the platelets to release their contents. Other activators include collagen, preferably 6–100 ug of monomer collagen per ml of buffer containing 10% platelets, ADP, preferably 2–10 u molar in said buffer, epinephrine, preferably 25–450 u molar in said buffer, and arachidonic acid, preferably 35–50 u molar in said buffer.

As a further alternative embodiment, PRP can be activated with thrombin or otherwise before centrifugation. The activated PRP can also be incorporated into liquid or paste preparations as described below.

In the preferred embodiment, the resulting supernatant was centrifuged at 950×g for about 5 minutes at about 4° C., thereby removing the released platelet ghosts and any fibrin contained in the suspension. The pellet formed by such centrifugation was discarded after the supernatant was extracted.

After removal of the platelet ghosts and fibrin, the remaining supernatant constitutes platelet releasate in platelet buffer, herein designated platelet releasate extract. The extract is frozen in 4 ml aliquots for storage or immediately used for assay or to make liquid or paste product as described below.

EXAMPLE 2

Platelet releasate extract may be prepared from platelets obtained from a blood bank or other source. Pheresis platelet concentrate may be obtained from a blood bank and immediately processed. One unit of platelets will yield approximately 200 mls of PRP.

The concentrate may be processed to produce the activated platelet suspension in the same manner as the anticoagulated patient blood sample is processed above, except that the PRP is centrifuged four times at 750×g for 10 minutes at about 4° C., resuspending the platelet pellet in platelet buffer after each centrifugation. After the fourth centrifugation, the platelet pellet is resuspended in platelet buffer to an approximate concentration of $10^9$ platelets/ml.

The platelet suspension is activated as described above and centrifuged at 950×g for 10 minutes at about 4° C. The supernatant is extracted and centrifuged at 10,000×g for 15 minutes at about 4° C. to remove residual platelets and any fibrin. The pellet is discarded after the supernatant is extracted. The supernatant which is the platelet releasate extract is frozen in 4 ml aliquots for storage or immediately used to make into liquid or paste preparations as described below.

As a further alternative to production from blood bank platelets, PRP produced from banked platelets can be directly activated before centrifugation.

EXAMPLE 3

Platelet releasate product is preferably administered to the patient in a liquid form. Platelet releasate extract, i.e. frozen platelet releasate in platelet buffer, may be thawed to room temperature. A measured volume of extract at room temperature may be added to a centrifuge tube so as to yield, after addition of platelet buffer to the centrifuge tube, a preferred dilution. 0.5 ml lidocaine may be added before adding platelet buffer. In this case, the buffer acts as the carrier. Also, the extract may in some cases be used without further dilution.

EXAMPLE 4

As an alternative embodiment, platelet releasate product may be applied in a paste form, comprising the extract in a carrier substance which is biologically compatible with and acts as a temporary "depot" for the active components of the supernatant. A macromolecular substance such as microcrystalline collagen, e.g. Avitene® brand microcrystalline collagen commercially available from Alcon Laboratories, Inc., Forth Worth, Tex. is a suitable carrier.

To prepare the paste platelet releasate product, the extract was thawed and diluted as above for the liquid form. Appropriate amounts of extract may be pipetted into a jar of Avitene microcrystalline collagen and mixed with a sterile pipette to achieve uniform consistency. Alternatively, extract may be mixed with the microcrystalline collagen.

The jars containing the resulting paste platelet releasate product should be capped and put into plastic bags with ice or frozen for transport or storage until applied to the patient.

EXAMPLE 5

In a wound treatment study in Florida, U.S.A. involving 102 nonhealing cutaneous wounds, autologous platelet releasate product was used to treat the wounds according to the above treatment procedures. The platelet releasate product was produced as follows: the platelet releasate extract, produced according to the procedures of Example 1, was further diluted 1:100 to form platelet releasate product. Prior to topical application of each of the platelet releasate products, an immunoassay for beta-thromboglobulin, available commercially from Diagnostica Stago, Asnieres-Sur-Seine, France as ASSERACHROM B-TG, was performed on the product corresponding platelet releasate extract to determine the amount of B-TG contained in the extract itself. The wounds were graded for functional assessment after completion of treatment. The amount of B-TG contained in the platelet releasate sample, which in this case was the extract, correlated to the success of the treatment by platelet releasate product as measured by the functional assessment:

Variables: B-TG VS FA
Sample Size: 102
Spearman R: 0.2427
T-value: 2.5023
2-Tail P: 0.014

FIG. 1 shows a representative plot of the data.

EXAMPLE 6

The foregoing example was repeated in a Kansas City, U.S.A. wound treatment study involving 86 wounds treated with autologous platelet releasate product. The amount of B-TG contained in the platelet releasate sample correlated to the functional assessment:

Variables: B-TG VS FA
Sample Size: 86
Spearman R: 0.3508
T-Value: 3.4328
2-Tail P: 0.0009

Figure 2:
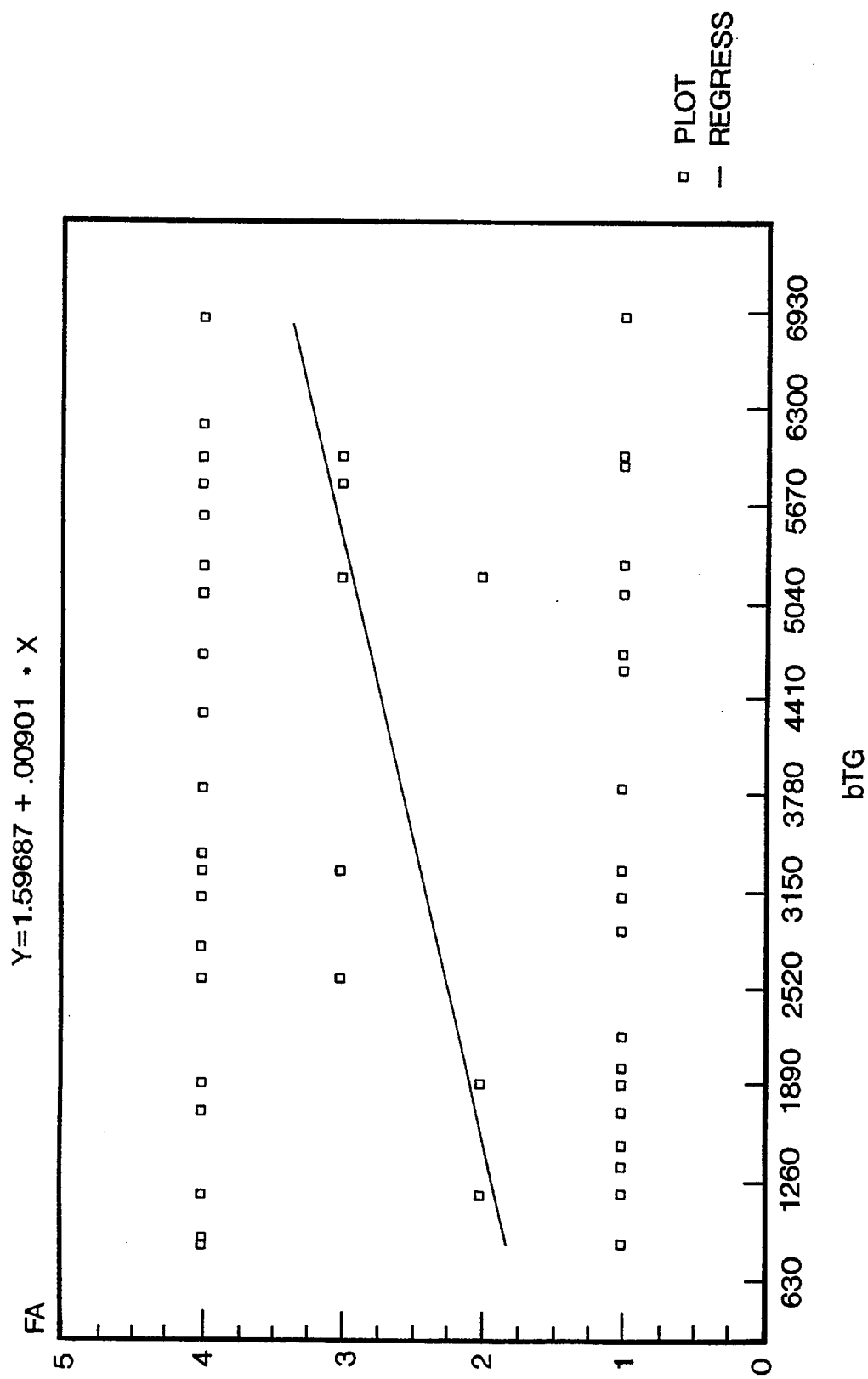
FIG. 2 shows a plot of functional assessment versus ng/ml of B-TG in platelet releasate extract in a Kansas City study.

FIG. 2 shows a representative plot of the data obtained.

EXAMPLE 7

Example 5 was again repeated at a Minnesota, U.S.A. wound treatment study involving 32 wounds treated with autologous platelet releasate product. The amount of B-TG contained in the platelet releasate sample correlated to the functional assessment:

Variables: B-TG VS FA
Sample Size: 32
Spearman R: 0.3629
T-Value: 2.1329
2-Tail P: 0.0412

Figure 3:
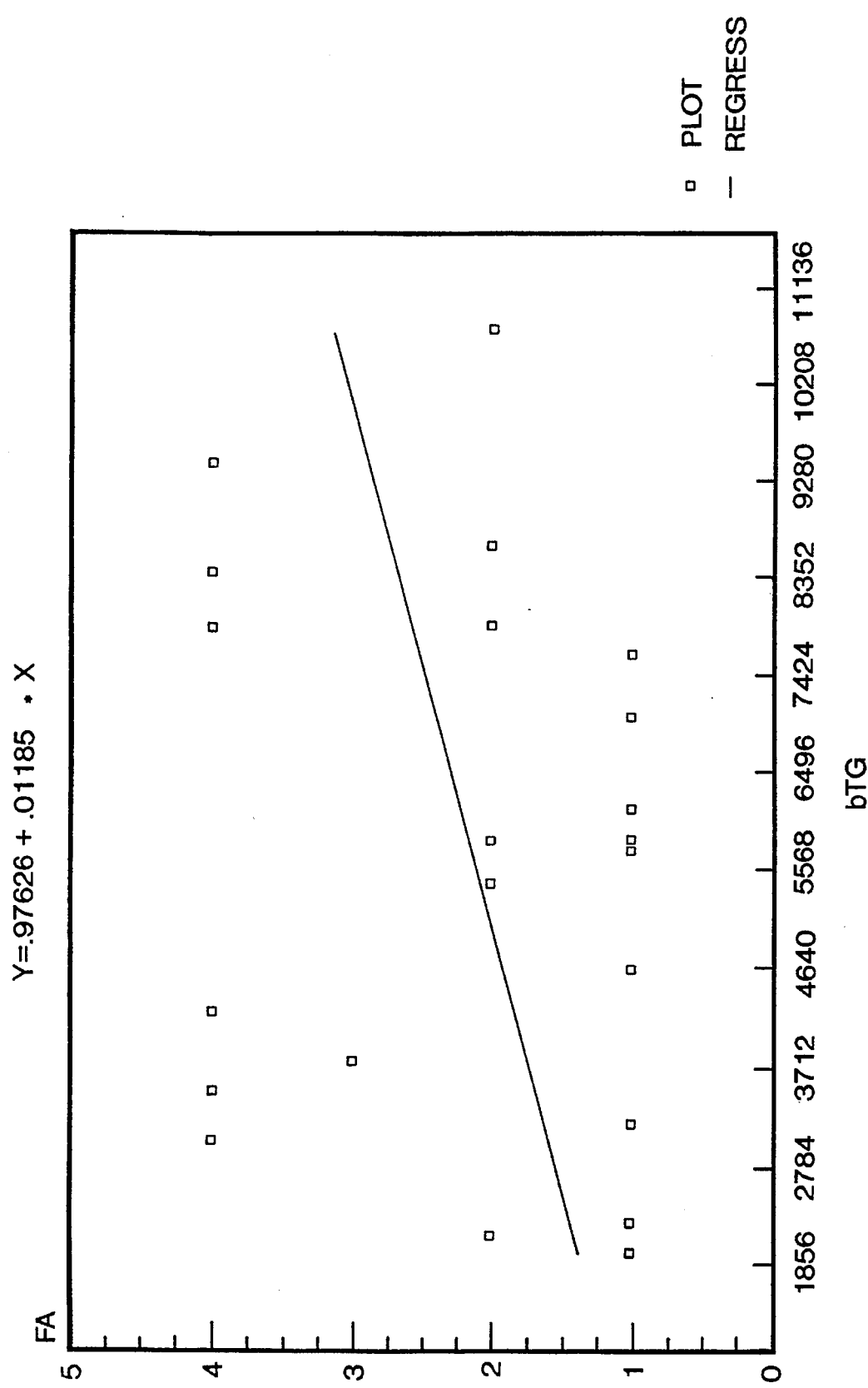
FIG. 3 shows a plot of functional assessment versus ng/ml of B-TG in platelet releasate extract in a Minnesota study.

FIG. 3 shows a representative plot of the data obtained.

Based on the foregoing examples of wound treatment, the success of wound treatment correlated to the amount of B-TG contained in the extract used to produce the product. Accordingly, platelet releasate product should preferably be manufactured to have a predetermined range of the amount of B-TG in the product. Since the product is composed of dilutions of platelet releasate extract, the amount of platelet releasate in form of extract or otherwise used to constitute the product should be adjusted to account for the amount of B-TG contained in the releasate extract. This manufacture procedure will enable the product to have a desired amount of B-TG in the product, even though the amount of B-TG in releasate varies from donor to donor and from time to time for a particular donor.

As illustrated by FIGS. 1–3, if an average FA grade of 2 or more is desired, the amount of B-TG should be at least about 25 ng per ml of product. Of course, B-TG amounts in excess of 66 ng per ml of product give optimal healing within the range of amounts of B-TG investigated by the studies.

Alternatively, other components of platelet releasate may be used to manufacture platelet releasate product containing minimal or optimal amount of platelet releasate. These components include, without limitation, PDGF, PDAF, PF-4, basic FGF, acidic FGF, TGF-2, TGF-B, PDEGF and fibronectin. Examples 8–9 show the correlation between B-TG and PF-4 and PDGF.

EXAMPLE 8

41 autologous platelet releasate samples were assayed for B-TG by the above B-TG immunoassay and for PF-4 by a PF-4 immunoassay available commercially from Diagnostica Stago as ASSERACHROM PF-4. The amount of B-TG in the platelet releasate sample correlated to the amount of PF-4 as follows:

Variables: B-TG VS PF-4
Sample Size: 41
Spearman R: 0.9148
T-Value: 14.1449
2-Tail P: <0.0001

Figure 4:
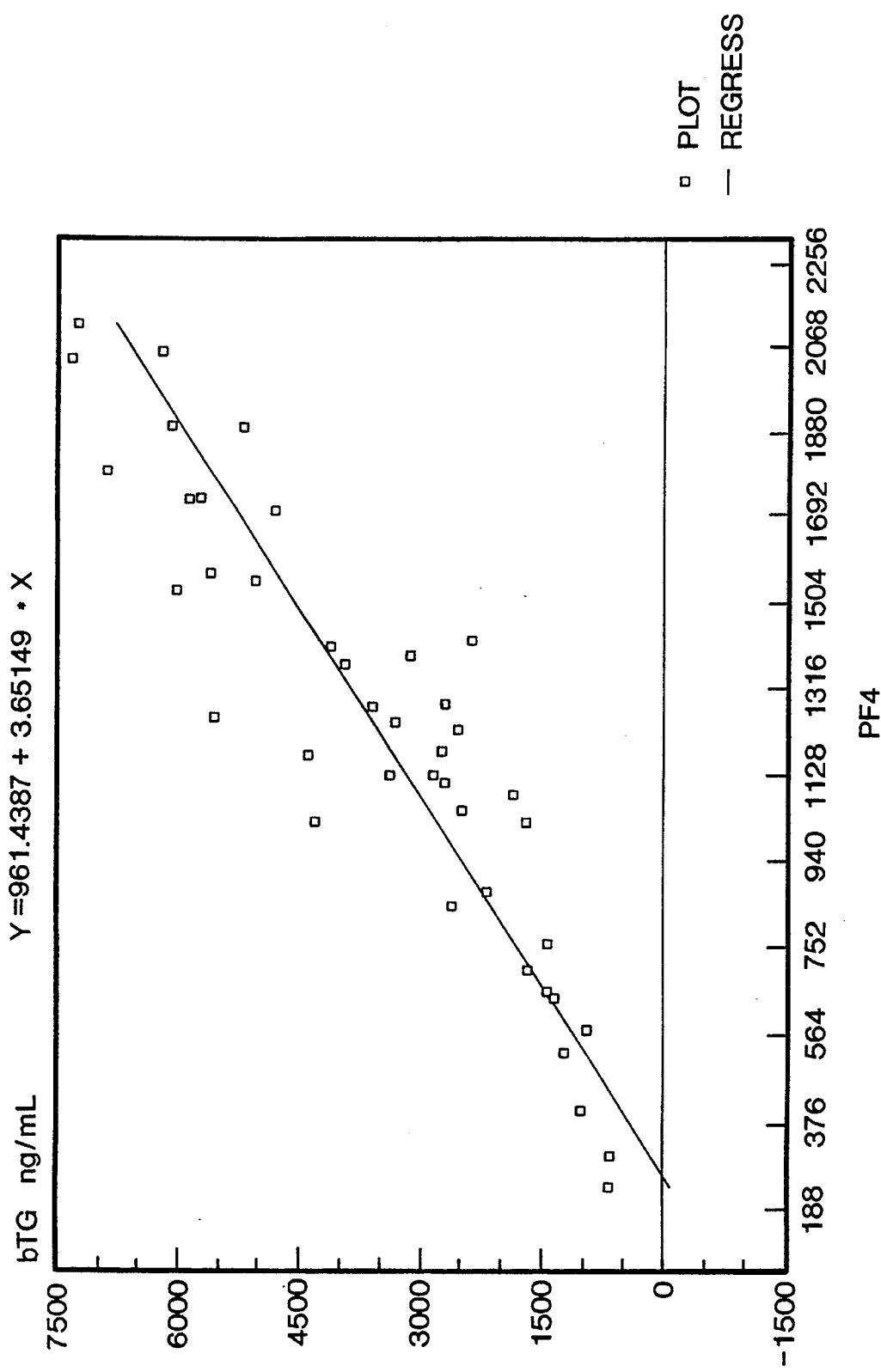
FIG. 4 shows a plot of B-TG versus PF-4 in platelet releasate extract.

FIG. 4 shows a representative plot of the data.

EXAMPLE 9

41 autologous platelet releasate samples were also assayed for B-TG according to the above B-TG assay and for PDGF according to the following assay protocol:

PDGF EIA PROTOCOL

DAY 1:
1. Block Reaction Plates (R) (Dynatech Imm-1, round bottom)
  a) Add 150 ul PT-20 (PBS TWEEN-20.05%) per well.
  b) Incubate R-plates for >60 min at 37° C. covered.
  c) Aspirate R-plates and dry. Go to step 3.
2. Coat Ouantitation Plates (O) (Dynatech Imm-2, flat bottom)
  a) Add 150 ul/well PDGFcsis (40 ng/ml in coating buffer).
  b) Incubate Q-plates overnight at 4° C. covered in ziplock bag.
3. After Blocking
  a) Make sample dilutions in PBA-T/20(PBS+1% BSA+ 0.05% T-20) using polypropylene tubes. Mix well.
4. Adding samples to R-plate
  a) Add 60 ul/well Goat Anti-PDGF (dil in PBA-T/20) at 2 ug/ml.
  b) Add 60 ul/well of diluted sample or standard.
  c) Incubate R-plates overnight at 4° C. covered in bag.
DAY 2:
1. O-plate Aspiration
  a) Aspirate Q-plate.
  b) Block Q-plate with 150 ul/well PT-20 (1–2 hrs, 37° C.).
  c) Aspirate, wash 3X, air dry.
2. R-plate Transfer
  a) Transfer contents of R-plates to Q-plates (100 u).
  b) Incubate Q-plates at room temp. for 30 min.
  c) Aspirate and wash.
3. Color Reaction
  a) Add 100 ul/well Rat ANTI-Goat-Peroxidase (1 ug/ml).
  b) Incubate 1 hr. at room temp.
  c) Aspirate and wash.
  d) Add 100 ul/well substrate (Tetramethylbenzidine).
  e) Read plates.

The amount of B-TG contained in the platelet releasate sample correlated to the amount of PDGF as follows:

Variables: B-TG VS PDGF
Sample Size: 41
Spearman R: 0.8103
T-Value: 8.6359
2-Tail P: <0.001

Figure 5:
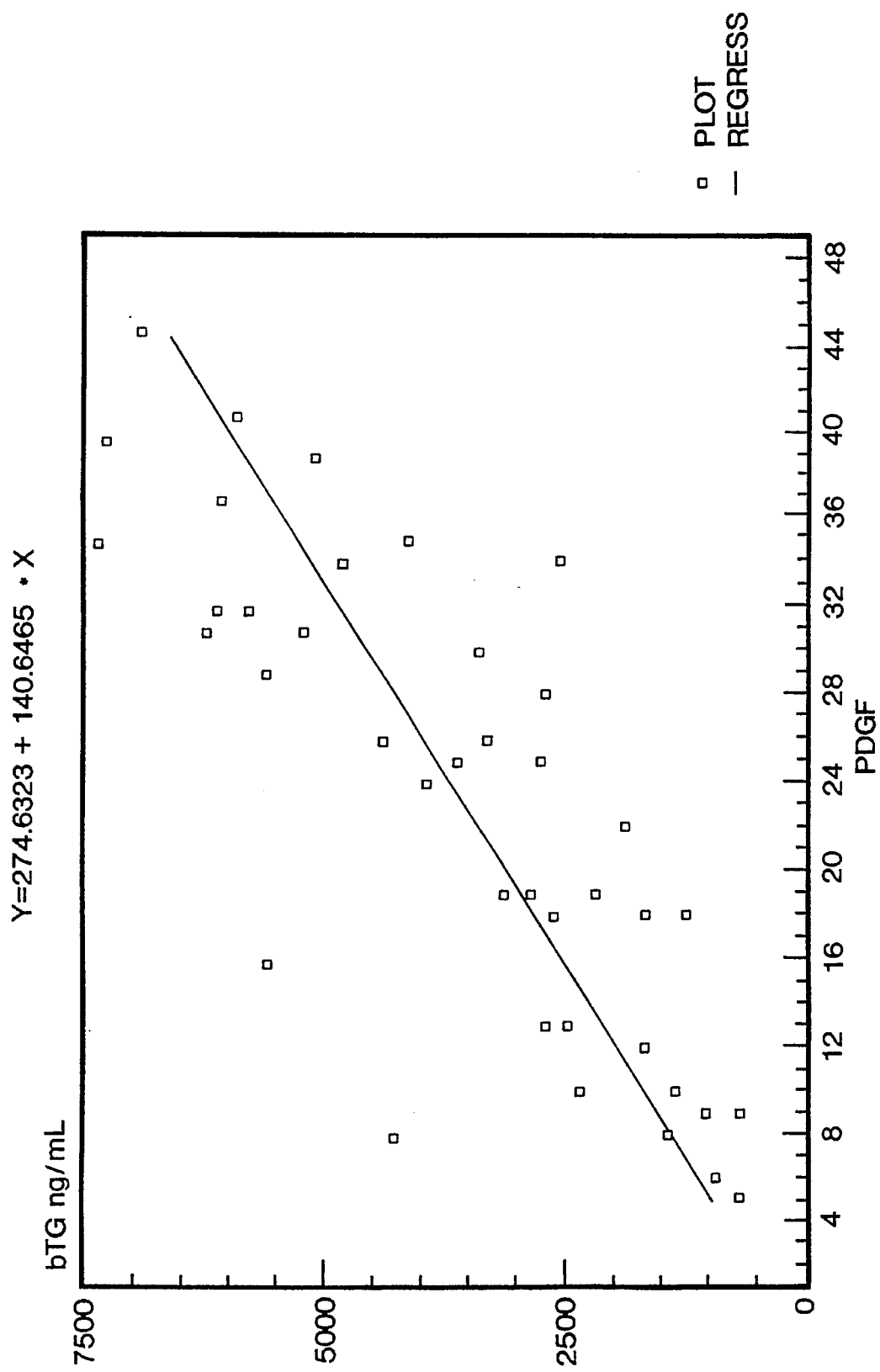
FIG. 5 shows a plot of B-TG versus PDGF in platelet releasate extract.

FIG. 5 shows a representative plot of the data.

As a further alternative, activities of platelet releasate may be used as the basis for manufacturing platelet releasate product containing a minimal or optimal amount of platelet releasate. These activities include, without limitation, fibroblast mitogenic activity ("FMA"), endothelial cell chemotaxis activity ("ECCA"), rabbit corneal assay activity ("RCAA") and keratinocyte cell chemotaxis activity ("KCCA"). Example 9 shows the correlation between B-TG and FMA, while examples 10–12 disclose assays defining the additional activities.

EXAMPLE 9

41 autologous platelet releasate samples were assayed for B-TG by the above B-TG immunoassay and for FMA by the following FMA protocol.

SET UP

1. Determine the number of microtiter plates necessary for FMA samples to be tested. (One plate will accommodate 24 quadruplicate or 32 triplicate samples "including" necessary controls).
2. Prepare approximately 20 ml per plate of Delbucco's Modified Eagle Medium (DMEM) containing 10% heat-inactivated calf serum (10% HI-CS). Prepare an additional 40 ml DMEM/10% HI-CS (used for preparing the cells).
3. Thaw out appropriate number of tubes of 3T3 (A31) fibroblasts, which are stored frozen in liquid nitrogen, in a 37° C. water bath. (Yield per tube will vary with frozen batch. Approximately 2,000,000 viable cells per microtiter plate will be needed.)
4. Aseptically transfer cells to sterile 50 ml culture tube (12 ml and 15 ml can also serve this purpose, just cut back on the liquid) containing 20 ml (5–10 ml) DMEM/10% HI-CS. "Resuspend well" and centrifuge at 450×g (1400 rpm in Mistral 3000i with shielded swing bucket rotors) for 10 minutes at R.T. Decant supernatant, resuspend cellular pellet in 10 ml DMEM/10% HI-CS, transferring it to a sterile 12 ml culture tube. Repeat centrifugation.
5. Resuspend cellular pellet in approximately 2–5 ml DMEM/10% HI-CS. Perform cell count.
6. Dilute the cells in DMEM/10% HI-CS to obtain a concentration of 200,000 cells per ml. (For each plate 10–11 mls are needed).
7. Add 100 ul per well to 96 well microtiter dish using an 8 or 12 multi-channel pipettor and sterile boat reservoir. Be sure to draw suspension in and out of the pipettor at least once per row to maintain cell-suspension adequately).

8. Add 100 ul DMEM/10% HI-CS to each well (for a combined total of 200 ul liquid per well).
9. Label plates with cell line and date of plate preparation. Incubate plates at 37° C., 5% $CO_2$ for 3 days or until fibroblasts are confluent.

MEDIA CHANGE/DAY 3

Three days after initiating the microtiter plates, the media needs to be changed to 0.8% HI-CS/DMEM to continue.

1. Examine the plates under the microscope to determine if the fibroblasts have grown to confluency. (There should be no gaps between cells). If cells are confluent, continue. If cells are not confluent, they can be grown for one extra day, or discarded.
2. Prepare 16 ml/plate 0.8% HI-CS/DMEM.
3. Open and place a sterile barrier sheet under hood. One at a time, take plates to sink and carefully flick all the liquid out of the plate in one clean, gentle sweep. Replace cover immediately.
4. Return quickly to sterile hood and gently blot opened plate on the sterile barrier to remove excess liquid.
5. Immediately and gently add 150 ul 0.8% HI-CS/DMEM per well using an 8 or 12 channel pipettor. Care must be taken to avoid disturbing the confluent cells as much as possible. Repeat steps 3 through 5 with next plate(s).
6. Incubate plates at 37° C., 5% $CO_2$ for 6 hours.
7. Retain excess 0.8% HI-CS for making dilutions.

STIMULATE CELLS/6 HRS. POST MEDIA CHANGE

Six hours after changing the media from 10% to 0.8% HI-CS, the cells are ready to be stimulated.

1. Fill out the template for each microtiter plate outlining the location of each control and sample to be tested.
2. Beginning in the upper left corner, the first 3 or 4 wells receive 50 ul of 0.8% HI-CS/DMEM only. (This serves as the plate background control).
3. The next 3 or 4 wells (working horizontally) receive both 20 ul undiluted HI-CS and 30 ul 0.8% HI-CS per well. (Final dilution therefore=10% HI-CS).
4. The next 3 or 4 wells receive 50 ul of Platelet Buffer control (10 ml Platelet Buffer+50 ul thrombin).
5. Add 50 ul of the test/control samples.
6. Incubate the plates 37° C. at 5% $CO_2$ for 18 hours. (Consistency in timing is important).

RADIOACTIVE LABELING

Eighteen hours after stimulation with test and control samples, the FMA microtiter plates are labeled with radioactive thymidine to demonstrate mitogenic activity.

1. Line work surface area with disposable paper liner to contain any accidental spills while working with the radionuclides. Protective gloves should be worn.
2. Prepare a 10 uCi [3H]-thymidine/ml DMEM solution as follows: Sterile transfer 0.5 cc [3H]-thymidine (NEN cat no. NET-027, 6.7 Ci mmol, 1 mCi/ml) to 49.5 ml DMEM (a 1/100 dilution).
3. Add 50 ul of [3H]-thymidine/DMEM solution to each well. Store leftover radioactive solution in the refrigerator for next time.
4. Properly discard pipette tips, gloves, dispensing container holding the aliquot of labeled media, and paper liner in the radioactive waste.
5. Label plates as radioactive and incubate in a tray to contain any spills at 37° C., 5% $CO_2$ for 6 hours.

HARVESTING

1. Carefully aspirate off radioactive culture media using a NUNC immuno wash. Be sure to use "raise pins" provided, to prevent contact of aspiration prongs with the cells.
2. Wash cells by adding 200 ul PBS with multi-channel pipettor. Aspirate with NUNC immuno wash.
3. Add 200 ul 0.25% trypsis/HBSS (Ca, Mg free) to each well. Incubate at 37° C., 5% $CO_2$ for 30 minutes.
4. Harvest plate onto glass filter paper using the Skatron Combi Cell Harvestor.
5. Immediately transfer wet filter paper discs into scintillation vials (Packard Pico Pro Vials) using the Skatron Filter Transfer apparatus.
6. Allow filter discs to dry overnight or in drying oven for 1–2 hours.

SCINTILLATION PREPARATION

1. Add 4 ml scintillation cocktail (Beckman Ready-Safe) to each vial.
2. Vials are capped tightly and shaken back and forth vigorously a few times to expose filter completely to the cocktail and dislodge potential air bubbles.

COATING

1. Place vials into the Beckman LS1701 green racks in order from left to right.
2. Place "program rack" into counter first, consisting of an empty green rack with ONE vial in the 18th position, telling the machine to use Program No. 1.
3. Program No. 1 is programmed as follows:
   Replicates: 3
   Count time: 2 minutes
   H#: No
   Sample Repeat: 1
   Data calc: CPM
   SCR: Yes
   RCM: Yes
   Vial size: Mini
   Count Blank: No
4. Place remaining racks into counter working "back to front" on the right side first, then "front to back" on the left side. Always end with the RED stop rack.
5. Push both "RESET" buttons at the same time.
6. When RESET is complete, and the printer has been checked for enough paper, press the START button and replace the cover.
7. Monitor the initial print-out to confirm accuracy of program being used.

Units of 1/ED-50 represents the dilution of the platelet releasate sample which results in a 50% stimulation of mitogenic activity in fibroblast 3T3 cells. For example, if a 0.25 or 1:4 dilution of the sample gave 50% stimulation, the I/ED-50 would be 4 units. Similarly, a 1:8 dilution would give an I/ED-50 of 8 units.

The amount of B-TG in the platelet releasate sample correlated to the FMA activity as follows:

Variables: B-TG VS FMA

Sample Size: 41

Spearman R: 0.7674

T-Value: 6.1927

2-Tail P: <0.0001

Figure 6:
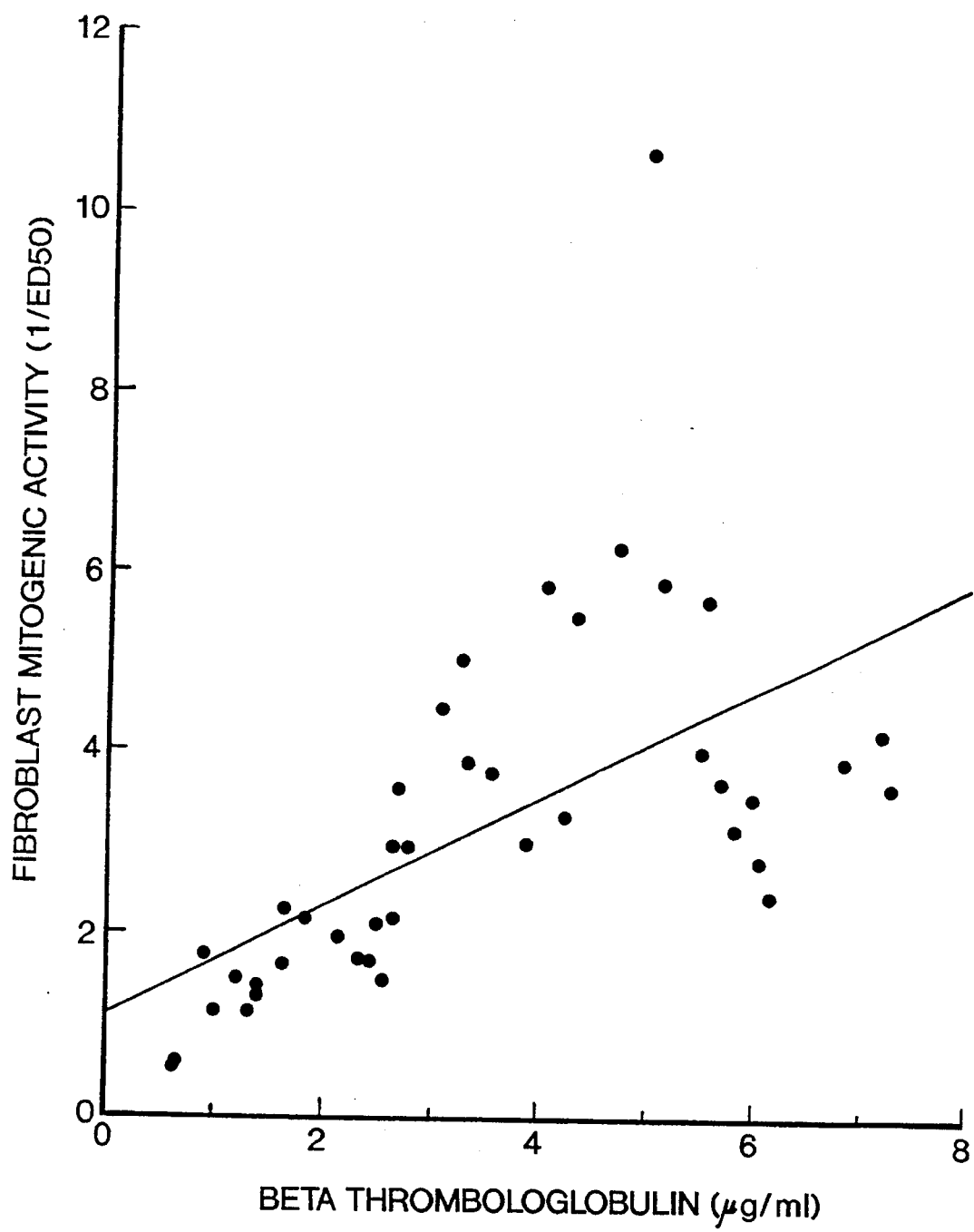
FIG. 6 shows a plot of B-TG versus FMA activity in platelet releasate extract.

FIG. 6 shows a representative plot of the data.

EXAMPLE 11

ECCA activity may be defined by the following protocol.

PREPARATION OF CELLS

1. Grow Rabbit Wound Capillary Endothelial (RWCE) to 60–85% "confluent" on 3–4 Primaria (Falcon #3824) 75 $cm^2$ flasks.
2. Approximately 20–24 hours before chemotaxis, remove the media and rinse flasks twice (2×) with HBSS* (Ca/Mg free, 6 ml/flask).
3. Remove last HBSS wash and add 12–15 ml (be consistent) of 0.2% lactalbumin in Media 199* to each flask. (This provides minimal nutrients and reduces serum induced stimulation, so the cells are ready to respond to the attractants.) Record time of media change on flask.
4. The following day, prepare the following:
    a) 50–100 ml 0.2% lactalbumin in M199 (LA-M199)
    b) 20–30 ml (5 ml/75 $cm^2$ flask) Enzyme Cocktail No. 2 (EC2-1×)* by diluting 1 ml EC2(10×) in 9 ml HBSS.
5. Remove 0.2% LA-M199 and rinse flask with 6–10 ml HBSS*. Immediately add 5 ml EC2(1×)* and incubate for exactly 14 minutes at R.T.
6. Pool EC2 from flasks into 50 ml polypropylene tube(s) containing at least 2 ml/flask 0.2% LA-M199, to help deactivate the enzymes. Immediately add 5 ml 0.2% LA-M199 to each flask.
7. Gently scrape off cells from bottom with a sterile cell scraper (American Scientific Products Cat. #T4206-1).
8. Add cells/media to the EC2 pool. For a final rinse, add 10 ml 0.2% LA-M199 to one flask. Transfer rinse wash from flask to flask, then pool with cells.
9. If final volume exceeds 40 ml, divide cells into two tubes for centrifugation. Centrifuge cells at 1400 rpm (approx. 450 g on Mistral 3000 centrifuge) for 10 minutes at R.T.
10. Discard supernatant by quickly pouring off. Resuspend pellet(s) in 8 ml total 0.2% LA-M199 (pool if divided) and transfer to a 15 ml centrifuge tube. Wash tubes with an additional 2 ml media and add to resuspended cells. Centrifuge at 1400 rpm for 10 minutes at R.T.
11. Resuspend cells in 2–5 ml 0.2% LA-M199 (adjust volume to size of pellet and estimated cell yield: to avoid recentrifugation) for counting.
12. Count cells:
    a) Add 30 ul cell suspension to 30 ul Trypan Blue.
    b) Load both sides of heamocytometer.
    c) Under 10×mag., count cells in eight 1 mm squares. Record number of viable (blue) cells. Do not count cells of abnormal size or shape.
    d) Multiply viable cell count by $2.5 \times 10^3$ to=cells per ml.
13. Adjust cell concentration to $0.75 \times 10^6$ cells/ml LA-M199 (i.e., 33,750 cells per/well in 45 ul). Approximately 2.25 ml/chamber is needed.
a) Example: There are 3 ml of $1.5 \times 10$ cells per ml. The final adjusted volume should be:

$$(3 \text{ ml})(1.5 \times 10^6 \text{ cells/ml}) = 5.95 \text{ ml } (0.75 \times 10^6 \text{ cells/ml})$$

Therefore, add 2.95 ml 0.2% LA-M199 to cells to obtain a final concentration of $0.75 \times 10^6$. In short, prepare 45 wells worth of cells/chamber at a concentration of 33,750 cells/45 ul 0.2% LA-M199/well.

*Suggested Volumes

| Flask 2 size ($cm^2$) | 0.2% LA-M199 feed media (ml) | HBSS wash (ml) | EC2(1X) (ml) |
|---|---|---|---|
| 25 | 5 | 5 | 3 |
| 75 | 15 | 6–10 | 5 |
| 150 | 30 | 10–15 | 10 |

PREPARATION OF FILTERS

1. Prepare 20 ml of 1 ug Fibronectin (Sigma #F4759)/1 ml HBSS (FN/HBSS) from frozen stock. Use polypropylene tips and tubes only for its preparation. (Example: Frozen stock=1 ng/ml $dH_2$-O-HBSS. Therefore dilute 200 ul stock in 19.8 ml HBSS). *Store on ice until use.
2. Use Nuclepore polypropylene filters (8.0 um pores, PVPF, from Neuro Probe Inc., 301-229-8598), one per chamber.
3. Cut the upper left-hand corner off the shiny side of the filter to provide filter orientation. *Use tweezers to handle the filter, (never fingers) and only at the ends.
4. Place 3–4 ml FN/HBSS in the center of a sterile petri dish. Lay filter on top of the FN/HBSS, shiny side down, allowing to spread beneath the filter; do not allow any FN/HBSS on the top of the filter.
5. Cover petri dish and allow to stand at R.T. for 30 minutes.
6. Carefully pour off FN/HBSS (by tilting majority to one side slowly, allowing filter to stick to plate, then pouring off completely), lift up filter, place 3–4 ml fresh FN/HBSS in center and repeat procedure on other side of filter (dull side down).
7. Coating is now complete and filters can be used.
    *Note:
    a) For consistency, use filter immediately, by timing the filling of the bottom chamber to coincide with the completion of coating the second side of the filter.
    b) When preparing two filters, it is recommended to stagger their coating times by 15 minutes to allow for the filling of one chamber before having to fill the second, to alleviate having to rush to fill both at the same time.

PREPARATION OF CHAMBERS

1. Remove Neuro Probe 48 well chemotaxis chambers from distilled water ($dH_2O$) storage bath. Rinse thoroughly with clean $dH_2O$. Dry top piece and gasket with tissue, and blow dry bottom piece with clean nitrogen gas.
2. Prepare test samples to load bottom of chamber. Each well holds approximately 26.0–26.5 ul) solution.
3. Add (approximately 26.1–26.5 ul) samples to the wells in the lower chamber.
    *Note:
    a) To produce a desired "positive meniscus", slight "topping off" with fluid may be necessary. This helps to counteract drying which occurs while filling the rest of the chamber. Avoid creating bubbles.
    b) Use a positive displacement pipette for best consistency. Since the first and last columns (A,L) of four wells on either chamber end are not utilized for chemotaxis, fill them with HBSS. Consequently, these same rows in the upper chamber are also filled with HBSS and not cells.

4. When the filters are ready, pour off FN/HBSS (as previously described). Carefully lift the filter off the petri dish; do not let either side scrape against the edge of the dish. By lifting filter slowly, the residual FN/HBSS on the filter is minimized. DO NOT drop or carelessly touch the filter at this point.

5. While holding both ends of the filter with forceps, lower the center of the filter onto the center of the chamber, then evenly cover bottom wells. The filter should be shiny side up

*Note:

Always orient chamber/filter consistently; i.e., always keep chamber trademark and cut corner on filter in the upper left-hand corner.

6. Only if necessary, adjust the filter slightly to properly align.
7. Lay the gasket just above the filter, but not touching.
8. Place the upper half of the chamber on top of gasket and push down both together. Hold them down tightly while securing the retaining screws.
9. Once secure, pick up chamber and look through wells for any bubbles that may have formed underneath filter; record these, as they can interfere with chemotaxis.
10. Add 45 ul HBSS to the four wells on both ends (A,L).
11. Next add 45 ul of cell suspension (i.e, $0.75 \times 10^6$ cells per ml) to the remaining wells.

*Note:

Add cells with pipette tip at an angle to prevent trapping air in the bottom. If a bubble forms, carefully withdraw liquid and refill. After filling, all wells should look uniform. If not, suspect trapped air and redo.

12. Place the chamber in a glass or polypropylene tray, add a water soaked gauze square (increasing humidity and preventing evaporation), and loosely cover with aluminum foil.
13. Incubate for 4 hours at 37° C., 5% $CO_2$.

REMOVAL AND WIPING OF FILTER

1. Etch a glass slide at one end with date and chamber number. Clean well with alcohol prep and dry.
2. Remove retaining nuts while holding down top plate.
3. Orient chamber with trademark in upper left-hand corner, over a paper towel.
4. Invert entire chamber (along horizontal axis) onto paper towel.
5. Push down on the four corners of the top plate so it stays parallel to the bottom plate as it drops. The filter should be stuck to the gasket.
6. Remove the bottom plate and immerse immediately in Tergazyme solution (¼ teaspoon Tergazyme/1000 ml $dH_2O$).
7. The "migrated cells" are now facing up. DO NOT disturb this face of the filter from here on.
8. Catch the very right-hand edge of the filter with forceps, lift edge to loosen, then pull filter slightly to the right so the end just hangs over the edge.
9. Clamp this end with the plastic clip and lift the filter off the gasket. Quickly apply the second plastic clip to the other end. Place top chamber piece immediately in Tergazyme.
10. Keeping the cell side up (ALWAYS), wet the non-migrated side in PBS. Do not let PBS wet the "migrated cells" side.
11. Holding the filter taut, draw the non-migrated side against the wiper blade (from one end to the next in one direction only.)
12. Repeat this procedure 4–5 times. Minimize time between wetting and wiping to prevent non-migrated cells from drying/sticking and causing incomplete removal. ALWAYS dry wiper blade before each successive wipe.
13. Place filter on appropriate etched slide, with cut corner on same end as etching, but on opposite side. Allow to dry overnight.
14. Rinse off chamber pieces sitting in Tergazyme with $dH_2O$ and store in fresh $dH_2O$, covered, until chambers are to be cleaned.

STAINING OF FILTER

Set up the Densitometer (LKB) so the filter can be read immediately after staining.

1. Place small black clip on the end of the dried filter/slide with the cut corner.
2. Stain in LeukoStat (Fisher brand) by dipping in each of three solutions, in order, 5 times for 5 seconds each time. Dab off excess stain on a paper towel or gauze between solutions.
3. Allow filter to sit in third stain for 30 seconds extra after the 5 dips.
4. Rinse filter in $dH_2O$ (use two changes of $dH_2O$). Dab excess $dH_2O$ off.
5. Place another clean glass slide (unmarked) directly over the filter, and press together carefully yet firmly, forcing out most of the air bubbles.
6. Read on the Densitometer.

DENSITOMETRY READING OF STAINED FILTER.

Allow Densitometer (LKB) to warm up for 10–20 minutes.
2. Place stained, wet slide on reading table and orient to proper coordinates as follows:

| Column | X Position | "Track" |
|---|---|---|
| B | 113.6 | 1 |
| C | 119.6 | 2 |
| D | 127.0 | 3 |
| E | 132.6 | 4 |
| F | 138.6 | 5 |
| G | 146.6 | 6 |
| H | 152.6 | 7 |
| I | 158.0 | 8 |
| J | 166.0 | 9 |
| K | 171.6 | 10 |

Additional densitometer settings:
a) Smoothing: 3
b) x-width: 4
c) y-start: 19
d) y-stop: 43

3. Line up slide. Check column positions.
4. Clip slide down without moving it.
5. Check "Y" coordinates on various rows.
6. Send ruler "home". "Ecs".
7. Close lid.
8. "Enter" (on computer), then "6" (or "Run") on Densitometer.
9. Calculate area of peaks from Densitometer using LKB's "GSXL" program.

CLEANING CHAMBERS

The following procedure is used to remove residual proteins, etc., from the chemotaxis chambers and gaskets. (Source: Terri Superdock, 118:61, Feb. 21, 1989).

1. Rinse dirty gaskets and chambers well with deionized water. Place chambers with corresponding gaskets in a 1 liter plastic beaker (2 sets/beaker).
2. Heat 0.75% Tergazyme solution (7.5 gm Tergazyme/1 liter dH$_2$O; 500–750 ml/2 chambers) to 50° C. DO NOT EXCEED 50° C.
3. Cover chambers and gaskets with 50° C. Tergazyme.
4. Place beaker(s) in a 50° C. waterbath. Cover bath and incubate for 2 hours.
   *For gasket cleaning see steps 10 and 11.
5. Remove chambers only and rinse well with dH$_2$O. Place chambers in a 1 liter plastic beaker (1000 ml); 2–3 chambers/beaker.
6. Cover chambers with R.T. 1M NaOH (600–700 ml/beaker). Cover beaker with tin foil.
7. Incubate beaker(s) in a 50° C. covered waterbath for 30 minutes.
8. Rinse chambers very well with dH$_2$O. Place chambers and a large stir bar in deep plastic tub. Strategically orient chambers (tops and bottoms) so as not to interfere with the spinning stir bar. Put tub on a magnetic stirrer near a sink.
9. Fill tub with dH$_2$O, letting it run continuously for 2 hours. Make sure the water is circulating adequately, and a syphoning system is placed in the tub leading to the sink to prevent overflow.
10. Place gaskets into one beaker with 0.75% Tergazyme and sonicate for 30 minutes.
11. Rinse well with dH$_2$O and place gaskets in 1 liter dH$_2$O. Sonicate for 2 hours, changing the water every 30 minutes.
12. Assemble chambers and gaskets (lightly tighten with screws) and place in flat pan (polypropylene) filled with fresh dH$_2$O. Cover with aluminum foil, and change water once a week.
13. Rinse chambers and gaskets well with fresh dH$_2$O before use.

EXAMPLE 12

KCCA activity may be defined by the following protocol.

PREPARATION OF CELLS

1. Obtain an EpiPack containing proliferating cells in T-25 Flask of Normal Human Epidermal Keratinocyte (NHEK), 500 ml bottles of KGM (Keratinocyte Growth Medium Supplemental and Serum Free), 500 ml bottle KBM (Keratinocyte Basal Medium) and subculture reagents consisting of HEPES Buffered Saline Solution Trypsin [(0.025% W/V)/EDTA (0.01% W/V)] solution Trypsin neutralizing solution from Clonetics Corporation, San Diego, Calif.
2. Upon arrival, unpack and incubate sealed T-25 flask at 37° C. 5% CO$_2$ to equilibrate temp.
3. Warm 5 ml KGM in sterile container.
4. Wipe T-25 flask thoroughly with 70% isopropyl alcohol under sterile field (Biohood).
5. Remove medium; discard in container containing a little bleach and replace with 5 ml warmed KGM. Leave cap screwed on but not tightly close.
6. Return to incubator @37° C., humidified with 5% CO$_2$ for 24–48 hours for subculturing. Do not allow cell culture to become confluent.

PASSING CELLS OFF T-25 FLASK

1. Under biohood, remove culture medium (discard in container with a little bleach) and wash cells with 2 ml HEPES buffered solution.
2. Remove HEPES add 2 ml Trypsin/EDTA Solution, let sit for 2 minutes.
3. Remove Trypsin/EDTA and place in sterile centrifuge tube containing 2 ml Trypsin Neutralizing Solution. Tighten cap on flask and look under scope.
4. Look for cells detaching and rounded up. After 3 additional min., hit flask against palm of hand once on one side and once on other side. Look under scope for cells floating. Do not go over 4 min. total since trypsinizing.
5. Under biohood, immediately add 2 ml Trypsin Neutralizing Solution and wash. Transfer cells to sterile centrifuge tube (see #3), rinse flask with another 2 ml of Trypsin Neutralizing Solution and place in centrifuge tube.
6. Check flask under scope; tighten cap to see if any cells are left.
7. If there are a lot of cells left, repeat entire procedure from step 1 and add to centrifuge tube. If there are no cells or very small amount, proceed to centrifuge tube.
8. Centrifuge cells at 220×G@25° C. for 10 min., discard supernate.
9. Resuspend cell pellet with warm 5 ml KGM and count with hemocytometer.
10. Inoculate new flask at desired density.

PASSING CELLS OFF T-75 flask (~70–80% CONFLUENT)

Follow same procedure for T-25 flask except use following amount:
   a. 5 ml HEPES buffered solution
   b. 7 ml Trypsin/EDTA solution
   c. Wash cells off flask with 7 ml Trypsin Neutralizing Solution, transfer to blue max tube.
   d. Wash flask again with 3 ml Trypsin Neutralizing Solution and place in blue max tube.
2. Centrifuge @220×G@25° C. for 10 min. Discard supernate.
3. Resuspend cell pellet with 5 ml KBM and place in centrifuge tube.
4. Centrifuge, discard supernate and resuspend with 2 ml KBM and count with hemocytometer.
5. Run chemotaxis assay and set up new densities.
NOTE:
1. For chemotaxis purposes, resuspend pellet with KBM.
2. For passing cells to set up new cell density only, use KGM.
3. Feed cells with fresh KGM M, W, F. To T-75 flask=15 ml KGM T-25 flask=5 ml KGM

PREPARATION OF CELL FOR CHEMOTAXIS

1. Trypsinize and spin down cells according to the procedure outlined under passing cells off T-75 flask.
2. Resuspend cells in KBM and count with a hemacytometer. Total cells=(Ave. count)×(ml KBM)×(trypan blue dilution)×($1\times10^4$).
3. Make final cell dilution of $5.56\times10^5$ cells/ml (or 25,000 cells/45 ul). Keep cells on ice until needed.

PREPARATION OF FILTER

1. Prepare 20 ml of 5 ug/ml Fibronectin solution (Sigma #F4759) from frozen stock. Use polypropylene sterile tip and tubes for its preparation. (Example: Frozen stock=0.1 mg/ml dH$_2$-HBSS. Therefore dilute 1,000 ul stock in 19.0 ml HBSS). Store on ice until used.

2. Use Nucleopore polypropylene filters (8.0 um pores, PVPF, from Neuro Probe Inc., 301-229-8598), one per chamber.
3. Cut the upper left-hand corner off the shiny side of the filter to provide filter orientation. *Use tweezers to handle the filter, (never fingers) and only at the ends.
4. Place 3–4 ml FN/HBSS in the center of a sterile petri dish. Lay filter on top of the FN/HBSS, shiny side down, allowing to spread beneath the filter; do not allow any FN/HBSS on the top of the filter.
5. Cover petri dish and allow to stand at R.T. for 30 minutes.
6. Carefully pour off FN/HBSS (by tilting majority to one side slowly, allowing filter to stick to plate, then pouring off completely), lift up filter, place 3–4 ml fresh FN/HBSS in center and repeat procedure on other side of filter (dull side down).
7. Coating is now complete and filters can be used.
   *NOTE:
   a) For consistency, use filter immediately, by timing the filling of the bottom chamber to coincide with the completion of coating the second side of the filter.
   b) When preparing two filters, it is recommended to stagger their coating times by 15 minutes to allow for the filling of one chamber before having to fill the second, to alleviate having to rush to fill both at the same time.

PREPARATION OF CHAMBERS

1. Remove Neuro Probe 48 well chemotaxis chambers from distilled water ($dH_2O$) storage bath. Rinse thoroughly with clean $dH_2O$. Dry top piece and gasket with tissue, and blow dry bottom piece with clean nitrogen gas.
2. Prepare test samples to load bottom of chamber. Each well holds approximately 26.0–26.5 ul) solution.
3. Add (approximately 26.1–26.5 ul) samples to the wells in the lower chamber.
   *NOTE:
   a) To produce a desired "positive meniscus", slight "topping off" with fluid may be necessary. This helps to counteract drying which occurs while filling the rest of the chamber. Avoid creating bubbles.
   b) Use a positive displacement pipette for best consistency. Since the first and last columns (A,L) of four wells on either chamber end are not utilized for cherootaxis, fill them with HBSS. Consequently, these same rows in the upper chamber are also filled with HBSS and not cells.
4. When the filters are ready, pour off FN/HBSS (as previously described). Carefully lift the filter off the petri dish; do not let either side scrape against the edge of the dish. By lifting filter slowly, the residual FN/HBSS on the filter is minimized. DO NOT drop or carelessly touch the filter at this point.
5. While holding both ends of the filter with forceps, lower the center of the filter onto the center of the chamber, then evenly cover bottom wells. The filter should be shiny side up
   *NOTE:
   Always orient chamber/filter consistently; i.e., always keep chamber trademark and cut corner on filter in the upper left-hand corner.
6. Only if necessary, adjust the filter slightly to properly align.
7. Lay the gasket just above the filter, but not touching.
8. Place the upper half of the chamber on top of gasket and push down both together. Hold them down tightly while securing the retaining screws.
9. Once secure, pick up chamber and look through wells for any bubbles that may have formed underneath filter; record these, as they can interfere with chemotaxis.
10. Add 45 ul HBSS to the four wells on both ends (A,L).
11. Next add 45 ul of cell suspension to the remaining wells.
    *NOTE:
    Add cells with pipette tip at an angle to prevent trapping air in the bottom. If a bubble forms, carefully withdraw liquid and refill. After filling, all wells should look uniform. If not, suspect trapped air and redo.
12. Place the chamber in a glass or polypropylene tray, add a water soaked gauze square (increasing humidity and preventing evaporation), and loosely cover with aluminum foil.
13. Incubate for 18 hours at 37° C., 5% $CO_2$.

REMOVAL AND WIPING OF FILTER

1. Etch a glass slide at one end with date and chamber number. Clean well with alcohol prep and dry.
2. Remove retaining nuts while holding down top plate.
3. Orient chamber with trademark in upper left-hand corner, over a paper towel.
4. Invert entire chamber (along horizontal axis) onto paper towel.
5. Push down on the four corners of the top plate so it stays parallel to the bottom plate as it drops. The filter should be stuck to the gasket.
6. Remove the bottom plate and immerse immediately in Tergazyme solution (¼ teaspoon Tergazyme/1000 ml $dH_2O$).
7. The "migrated cells" are now facing up. DO NOT disturb this face of the filter from here on.
8. Catch the very right-hand edge of the filter with forceps, lift edge to loosen, then pull filter slightly to the right so the end just hangs over the edge.
9. Clamp this end with the plastic clip and lift the filter off the gasket. Quickly apply the second plastic clip to the other end. Place top chamber piece immediately in Tergazyme.
10. Keeping the cell side up (ALWAYS), wet the nonmigrated side in PBS. Do not let PBS wet the "migrated cells" side.
11. Holding the filter taut, draw the non-migrated side against the wiper blade (from one end to the next in one direction only).
12. Repeat this procedure 4–5 times. Minimize time between wetting and wiping to prevent non-migrated cells from drying/sticking and causing incomplete removal. ALWAYS dry wiper blade before each successive wipe.
13. Place filter on appropriate etched slide, with cut corner on same end as etching, but on opposite side. Allow to dry overnight.
14. Rinse off chamber pieces sitting in Tergazyme with $dH_2O$ and store in fresh $dH_2O$, covered, until chambers are to be cleaned.

STAINING OF FILTER

Set up the Densitometer (LKB) so the filter can be read immediately after staining.
1. Place small black clip on the end of the dried filter/slide with the cut corner.
2. Stain in LeukoStat (Fisher brand) by dipping in each of three solutions, in order, 5 times for 5 seconds each time. Dab off excess stain on a paper towel or gauze between solutions.

3. Allow filter to sit in third stain for 30 seconds extra after the 5 dips.
4. Rinse filter in dH$_2$O (use two changes of dH$_2$O). Dab excess dH$_2$O off.
5. Place another clean glass slide (unmarked) directly over the filter, and press together carefully yet firmly, forcing out most of the air bubbles.
6. Read on the Densitometer.

DENSITOMETRY READING OF STAINED FILTER

1. Allow Densitometer (LKB) to warm up for 10–20 minutes.
2. Place stained, wet slide on reading table and orient to proper coordinates as follows:

| Column | X Position | "Track" |
| --- | --- | --- |
| B | 113.6 | 1 |
| C | 119.6 | 2 |
| D | 127.0 | 3 |
| E | 132.6 | 4 |
| F | 138.6 | 5 |
| G | 146.6 | 6 |
| H | 152.6 | 7 |
| I | 158.0 | 8 |
| J | 166.0 | 9 |
| K | 171.6 | 10 |

Additional densitometer settings:
 a) Smoothing: 3
 b) x-width: 4
 c) y-start: 19
 d) y-stop: 43
3. Line up slide. Check column positions.
4. Clip slide down without moving it.
5. Check "Y" coordinates on various rows.
6. Send ruler "home". "Ecs".
7. Close lid.
8. "Enter" (on computer), then "6" (or "Run") on Densitometer.
9. Calculate area of peaks from Densitometer using LKB's "GSXL" program.

CLEANING CHAMBERS

The following procedure is used to remove residual proteins, etc., from the chemotaxis chambers and gaskets. (Source: Terri Superdock, 118:61, Feb. 21, 1989).
1. Rinse dirty gaskets and chambers well with deionized water. Place chambers with corresponding gaskets in a 1 liter plastic beaker (2 sets/beaker).
2. Heat 0.75% Tergazyme solution (7.5 gm Tergazyme/1 liter dH$_2$O; 500–750 ml/2 chambers) to 50° C. DO NOT EXCEED 50° C.
3. Cover chambers and gaskets with 50° C. Tergazyme.
4. Place beaker(s) in a 50° C. waterbath. Cover bath and incubate for 2 hours.
*For gasket cleaning see steps 10 and 11.
5. Remove chambers only and rinse well with dH$_2$O. Place chambers in a 1 liter plastic beaker (1000 ml); 2–3 chambers/beaker.
6. Cover chambers with R.T. 1M NaOH (600–700 ml/beaker). Cover beaker with tin foil.
7. Incubate beaker(s) in a 50° C. covered waterbath for 30 minutes.
8. Rinse chambers very well with dH$_2$O. Place chambers and a large stir bar in deep plastic tub. Strategically orient chambers (tops and bottoms) so as not to interfere with the spinning stir bar. Put tub on a magnetic stirrer near a sink.
9. Fill tub with dH$_2$O, letting it run continuously for 2 hours. Make sure the water is circulating adequately, and a syphoning system is placed in the tub leading to the sink to prevent overflow.
10. Place gaskets into one beaker with 0.75% Tergazyme and sonicate for 30 minutes.
11. Rinse well with dH$_2$O and place gaskets in 1 liter dH$_2$O. Sonicate for 2 hours, changing the water every 30 minutes.
12. Assemble chambers and gaskets (lightly tighten with screws) and place in flat pan (polypropylene) filled with fresh dH$_2$O. Cover with aluminum foil, and change water once a week.
13. Rinse chambers and gaskets well with fresh dH$_2$O before use.

EXAMPLE 13

RCAA activity may be defined by the following protocol.

2–4 polymer pellets are made for each sample to be tested for angiogenic activity. A solution of 10% v/v polymer, available as Hydron® polymer, type NCC, cell culture grade, (available commercially from HydroMed Sciences, New Brunswick, N.J. 08901), 1% v/v polyethyleneglycol in 70% v/v ethanol should be prepared (hereinafter polymer solution). Polymer solution is mixed 1:1 v/v with test sample. A piece of plastic autoclave bag is taped onto a flat surface, making sure it is taut. The surface is then wiped off with an alcohol prep, and allowed to dry. 20 ul of the 1:1 mixture is dropped onto the plastic. The polymer pellets are then dried under vacuum for approximately 2 hours, or until dry.

The corneal implant assay is conducted on a 4–6 lb. New Zealand White Rabbit. Anesthetic is prepared by mixing 1:1 v/v Ketamine hydrochloride 100 mg/ml, commercially available as Ketaset® from Veterinary Products, Bristol Laboratories, Syracuse, N.Y. 13201, and acepromazine maleate 10 mg/ml, commercially available as Promace® from Aveco Co., Inc., Fort Dodge, Iowa 50501, in the same syringe. 4–5 cc is used for each rabbit. Anesthetic is injected into the gluteus maximum or gastrocnemeus using a 23 gauge needle, gently rubbing the area after injection. The rabbit is properly anesthetized when it cannot resist being rolled onto its back, usually in 10–15 minutes.

The rabbit is placed on a sterile drape. 3–5 drops of proparacine hydrochloride 0.5%, commercially available as Ophthetic® from Allergan Pharmaceuticals, Inc., Irvine, Calif. 92713, are put in each eye to numb the area. The anesthetic solution is used as needed throughout the procedure whenever the eye becomes dry.

The eye is brought out of the socket using petite point tissue forceps. The forceps are slowly worked towards the inner corner of the eye and a bit of tissue is clamped to ensure the eye remains in this position while working, taking care not to clamp the optic nerve.

A scalpel, Beaver eye blade No. 5210, commercially available from Beaver Surgical Products, Waltham, Mass. 02154, is gently drawn across the apex of the cornea, making an incision approximately 3.0 mm long. It is possible to puncture the cornea which will cause the aqueous humor to seep through. If this should occur, the animal must be sacrificed.

With a Elschnig cyclodialysis spatula, 1 mm wide, 10 mm long commercially available from U. Mueller, Chicago, Ill. 60648, product #OP-2040, a canal is gently made through the cornea towards the capillary bed, stopping approximately 2 mm from the capillary bed. A "pocket" is made for the polymer pellet by moving the tip of a probe side to side, taking care not to move the probe forward as the pellet should not be closer than 1 mm to the capillary bed. A polymer pellet is lifted off the plastic using forceps and placed on the eye at the point of incision. With a spatula, the pellet is pushed through the canal and into the pocket. Several drops of anesthetic solution is used to lubricate the area and make insertion of the pellet easier. The pellet must be concentrated in the pocket. Trapped air is pushed out from the pocket by drawing a spatula along the canal on the outside of the cornea.

The forceps are then unfastened. The eyelids are gently pulled up and out manually and the eye resumes its normal position. Three drops of anti-bacterial solution, commercially available as Neosporin® Opthalmic Solution from Burroughs Wellcome Co., Research Triangle Park, N.C. 27709, are put into each eye to minimize the possibility of infection.

One rabbit is used for each sample to be tested (i.e., 2 pellets of same sample per rabbit, one in each eye).

Eyes are checked on days 3, 5 and 7 for any direct growth of capillaries towards the pellet and graded according to the method of Gimbrone et al., J. Natl. Cancer Inst. 52:413–427(1974), and Banda et al., U.S. Pat. No. 4,503,038, both of which are incorporated in their entirety by reference. Pictures of eyes are taken on day 7 to record capillary growth. Accordingly, the invention may be embodied in other specific forms without departing from the spirit or essential characteristics thereof. From the foregoing, it will be obvious to those skilled in the art that various modifications in the above-described methods and techniques can be made without departing from the spirit or scope of the invention.

We claim:

1. A method of making a product for efficacious topical cutaneous wound healing, said product comprising an amount of platelet releasate, said amount determined by: performing an assay on a platelet releasate sample to determine the amount in said sample of beta-thromboglobulin or at least one wound healing factor, wherein the factor has a concentration in the releasate that correlates with that of beta-thromboglobulin; based on said assay calculating the amount of platelet releasate containing the amount of the beta-thromboglobulin or said at least one wound healing factor necessary to achieve a predetermined degree of efficacious topical cutaneous wound healing; and incorporating said amount of platelet releasate into said product for efficacious topical cutaneous wound healing.

2. The method of claim 1 wherein said at least one wound healing factor is selected from the group consisting of platelet derived growth factor, platelet derived angiogenesis factor, platelet factor 4, basic fibroblast growth factor, acidic fibroblast growth factor, transforming growth factor alpha, transforming growth factor beta, platelet derived epidermal growth factor and fibronectin.

3. The method of claim 2 wherein said at least one wound healing factor is beta-thromboglobulin.

4. The method of claim 3 wherein the platelet releasate product contains beta-thromboglobulin at a concentration of greater than about 25 nanograms per milliliter of platelet releasate product.

5. The method of claim 2 wherein said at least one wound healing factor is platelet derived growth factor.

6. The method of claim 5 wherein the platelet releasate product contains platelet derived growth factor at a concentration greater than about 0.2 nanograms per milliliter of a platelet releasate product.

7. The method of claim 2 wherein said at least one wound healing factor is platelet factor 4.

8. The method of claim 7 wherein the platelet releasate product contains platelet factor 4 at a concentration greater than about 10 nanograms per milliliter of a platelet releasate product.

9. The method of claim 2 wherein said at least one wound healing factor is platelet derived angiogenesis factor.

10. The method of claim 1 wherein said predetermined amount of said at least one wound healing factor is sufficient to cause efficacy of cutaneous wound healing at least equivalent to grade 2 functional assessment score.

11. The method of claim 1 wherein said assay detects an activity selected from the group consisting of fibroblast mitogenic activity, endothelial cell chemotaxis activity, rabbit corneal assay activity and keratinocyte cell chemotaxis activity.

12. The method of claim 11 wherein the activity is fibroblast mitogenic activity.

13. The method of claim 12 wherein the platelet releasate product has a fibroblast mitogenic activity greater than about 2.51/ED-50 units per milliliter of platelet releasate product.

* * * * *